United States Patent [19]

Boucher

[11] Patent Number: 5,004,757
[45] Date of Patent: Apr. 2, 1991

[54] VIRUCIDAL LOW TOXICITY COMPOSITIONS

[75] Inventor: Raymond M. G. Boucher, Houston, Tex.

[73] Assignee: Wave Energy Systems, Inc., Houston, Tex.

[21] Appl. No.: 286,738

[22] Filed: Dec. 20, 1988

[51] Int. Cl.$^5$ .................. A61K 31/115; A61K 31/11
[52] U.S. Cl. .................... 514/694; 514/696; 514/697; 514/698; 514/705; 514/934
[58] Field of Search .............. 514/694, 696, 697, 705, 514/698

[56] References Cited

U.S. PATENT DOCUMENTS

| | | | |
|---|---|---|---|
| 2,801,216 | 7/1957 | Yoder | 514/765 |
| 3,079,985 | 3/1963 | Boehne | 154/48.1 |
| 3,886,269 | 5/1975 | Trujillo | 514/694 X |
| 3,917,850 | 11/1975 | Boucher | 514/765 |
| 3,968,248 | 7/1976 | Boucher | 514/705 |
| 3,968,250 | 7/1976 | Boucher | 514/705 |
| 3,983,252 | 9/1976 | Buchalter | 514/698 |
| 4,048,336 | 9/1977 | Winicov et al. | 514/694 |
| 4,093,744 | 6/1978 | Winicov et al. | 514/705 |
| 4,436,754 | 3/1984 | Jacobs | 514/694 |
| 4,859,186 | 8/1989 | Ranly | 433/228.1 |

OTHER PUBLICATIONS

Kabara, ed., Cosmetic and Drug Preservation, pp. 649–650.
Sidwell, R. W., "Potentially Infectious Agents Associated With Shearling Bed Pads", *Applied Microbiology*, Jan. 1970, pp. 53–59.

*Primary Examiner*—John W. Rollins
*Attorney, Agent, or Firm*—Pravel, Gambrell, Hewitt, Kimball & Krieger

[57] ABSTRACT

Very potent, stable, odorless, and phenol-free virciudal solutions are active at high dilution when used for surface decontamination of animate and inanimate objects. The virucidal compositions described are efficacious in a matter of minutes against both the lipophilic and the more resistant hydrophilic viruses. The three active ingredients in these virucidal compositions are the glutaraldehyde monomer in equilibrium with its hydrates and polymers, hydrogen-bonded glycol molecules to eliminate aldehydes odor, and an anionic surfactant of the alkyl sulfate, alkyl sulfonate, alcohol sulfate or alkyl aryl sulfonate type. A preferred anionic surfactant would be the Sodium Dodecyl Sulfate (SDS), which exhibits strong cidal synergism against the Herpes Simplex Virus type 1 when mixed at a concentration as low as 0.0005% in diluted glutaraldehyde aqueous solutions (0.0025%). Improved virucidal killing at higher dilutions of the same formula were observed with the more resistant Coxsackie B viruses. Because of the low concentration of active ingredients, these solutions exhibit a very low toxicity, making them suitable for topical applications as antiseptics.

16 Claims, 2 Drawing Sheets

METHANOL (FORMALDEHYDE) AND POLYMERS IN AQUEOUS SOLUTION

FORMALDEHYDE MONOMER      METHYLENE GLYCOL     POLYOXYMETHYLENE GLYCOL POLYMERS

GLUTARALDEHYDE AND POLYMERS IN AQUEOUS SOLUTION

VIRUCIDAL LOW TOXICITY COMPOSITIONS

FIELD OF THE INVENTION

This invention relates to virucidal compositions and, more particularly, to glutaraldehyde containing compositions which are phenol-free, odorless, stable and potent at very high dilutions against lipophilic and hydrophilic viruses.

BACKGROUND OF THE INVENTION

There is a need for virucidal compositions which contain a minimum amount of active chemicals providing low toxicity, but which provide a fast and complete kill of resistant viruses on animate and inanimate surfaces. Very few chemical disinfectants are effective against resistant viruses when used at low concentrations in the range of from about 0.006% to 0.00125% (wt/vol.).

To measure the virucidal effectiveness of compositions, the work of Noll and Younger (Virology 8:319-343, 1959) suggested classifying viruses based on their affinity for lipids. Those viruses which easily combine with lipids, such as cholesterol, were called "lipophilic". Viruses which did not readily combine with lipids were called "hydrophilic". In 1963, Klein and Deforest (Proceedings, 49th meeting of Chem. Spec. Manuf. Assoc., page 116-118, New York) conducted a thorough investigation of the behavior of different types of viruses with several disinfectants. They found that the resistance of hydrophilic viruses to some germicides was based upon the failure of these germicides to react with hydrophilic viruses. Lipophilic viruses, on the other hand, were more susceptible to the inactivation of lipophilic germicides. Using three resistant hydrophilic viruses (Poliovirus Type 1, Coxsackie-virus B1 and Echovirus 6) and four lipophilic viruses (Adenovirus Type 2, Herpes Simplex virus Type Vacciniavirus and Asian Influenza virus), Klein and Deforest determined the lowest concentrations of germicides needed to inactivate these viruses in 10 minutes. Table 1 shows their results pertaining to the most resistant virus (Poliovirus Type I).

TABLE I

| LOWEST CONCENTRATIONS (wt/vol. %) OF DISINFECTANTS INACTIVATING THE POLIOVIRUS TYPE 1 IN 10 MINUTES* | | |
|---|---|---|
| Sodium hypochlorite | 0.02 | |
| Iodophor | 0.015 | |
| Bichloride of mercury | 0.2 | |
| Formalin | 8.0 | |
| Glutaraldehyde | 2.0 | |
| Ethyl Alcohol | 70.0 | |
| Isopropyl Alcohol | 95.0 | |
| Phenol | 5.0 | |
| O-Phenyl Phenol | 12.0 | (neg.) |
| Quaternary Ammonium | 10.0 | (24 hrs. contact neg.) |

As previously demonstrated by Klein and Deforest (see Table I), phenols or phenol compounds such as ortho phenylphenol have little or no activity against hydrophilic viruses. In their study, Klein and Deforest showed, for instance, that an orthophenyl phenol concentration as high as 12% did not even kill the following viruses: Polio type 1, Coxsackie B-1 and Echo 6. Phenol itself needed concentrations as high as 5% to be active against the same three hydrophilic viruses. More recently, an independent laboratory study (Hazelton Biotech Corp., Project No. 2288-100, June 26, 1984), confirmed that a mixture of phenol with sodium phenate containing 0.51% of these compounds could not kill the Polio virus type 1, ATCC VR 192, according to EPA standards (DIS/TSS-7, Nov. 1981). It is apparent that high concentration of phenols or phenol compounds are needed to act upon resistant viruses. Conversely, phenol, phenol salts or phenolic compounds in the 0.5 to 5% concentration range are very toxic. Local damages to the skin include eczema, inflammation, discoloration, papillomas, necrosis, sloughing and gangrene (see Industrial Hygiene and Toxicology, Vol. 2, 1363-1408, second edition, Interscience Publishers, 1963). Monohalogenated phenols, or methyl phenols, or dimethyl phenols were shown to be as potent in promoting papillomas in animals as phenol itself Polychlorinated Biphenyls (PCB) have been banned by the EPA because they are extremely toxic even at low levels of concentration in the food chain.

More recently, other minimum germicide concentrations needed for inactivation in 10 minutes were determined (Journ. Hosp. Supp. Process. Distrib., Jan. 1985, pages 40-47) with Poliovirus Type 1 and 2. This data was collected by Dr. J. Bednarz-Prashad (University of Texas Medical School, Houston) using the standardized AOAC virucidal test approved by the Environmental Protection Agency (EPA Notice, DIS/TSS-7, Nov. 12, 1981). The results of this study showing the minimum concentration required to inactivate the virus with a 10-minute contact time are listed in Table II.

TABLE II

| MINIMUM CONCENTRATION (wt/vol. %) TO INACTIVATE POLIOVIRUSES IN 10 MIN. (AOAC METHOD) | |
|---|---|
| Chlorhexidine gluconate | >0.5* |
| Glutaraldehyde + non-ionic | 0.25 |
| Glutaraldehyde + non-ionic + Glycol | 0.19 |
| O-Phenyl Phenol | >1.0* |
| Glutaraldehyde-phenate | >0.14* |

*This represents the lowest concentration of commercial product tested, virus was not inactivated at this concentration.

The minimum concentration of glutaraldehyde was eight times lower in Prashad's experiments than in Klein and Deforest's because Prashad used a glutaraldehyde activated by small amounts of non-ionic ethoxylates of isomeric linear alcohols (e.g, TERGITOL 15-S-12). In other words, as described in U.S. Pat. No. 3,968,248, and demonstrated by R. M. G. Boucher (Am. Journ. Hosp. Pharm. 31: 546-557, June 1974), the presence of small quantities of non-ionic surfactants can, in some cases, increase the cidal activity of glutaraldehyde solutions. Triethylene glycol was added to this same formula to make it odorless, and this glycolcontaining composition permitted a minimum glutaraldehyde concentration of 0.19% (wt/vol). This concentration is very close to the value observed using the glutaraldehyde solution containing the non-ionic ethoxylates without glycol. These prior results demonstrate a need for compositions exhibiting greater virucidal activity at low, relatively non-toxic, concentrations.

It is, therefore, an objection of the present invention to produce more potent virucidal solutions and decrease the amount of dialdehyde needed to destroy typical, lipophilic or hydrophilic viruses.

It is a further objective of the present invention to provide patent virucidal solutions which are formulated without phenols.

SUMMARY OF THE INVENTION

It has been discovered that potent novel virucidal compositions are created by the synergistic combination of glutaraldehyde monomer in equilibrium with its hydrates and polymers; together with hydrogen-bonded glycol molecules and an anionic surfactant selected from the group of anionic surfactant types including alkyl sulfate, alkyl sulfonate, alcohol sulfate and alkyl aryl sulfonate. In particular, sodium dodecyl sulfate is preferred. Such compositions are effective against both lipophilic and hydrophilic viruses, exhibiting strong cidal synergism against Herpes Simplex Virus Type 1 and improved virucidal activity against Coxsackie B viruses. The virucidal compositions of this invention are effective in very dilute aqueous glutaraldehyde solutions, i.e., 0.0025% (wt/vol.), with the anionic surfactant being present in concentrations as low as 0.0005% by (wt/vol.). Further, the practice of adding glycol molecules to glutaraldehyde compositions to deodorize the composition is shown in U.S. Pat. No. 3,886,269, which is incorporated herein by reference in its entirety. Adopting this practice does not deleteriously affect the virucidal efficacy of the composition of the present invention.

DETAILED DESCRIPTION OF THE DRAWINGS

Figure 1:
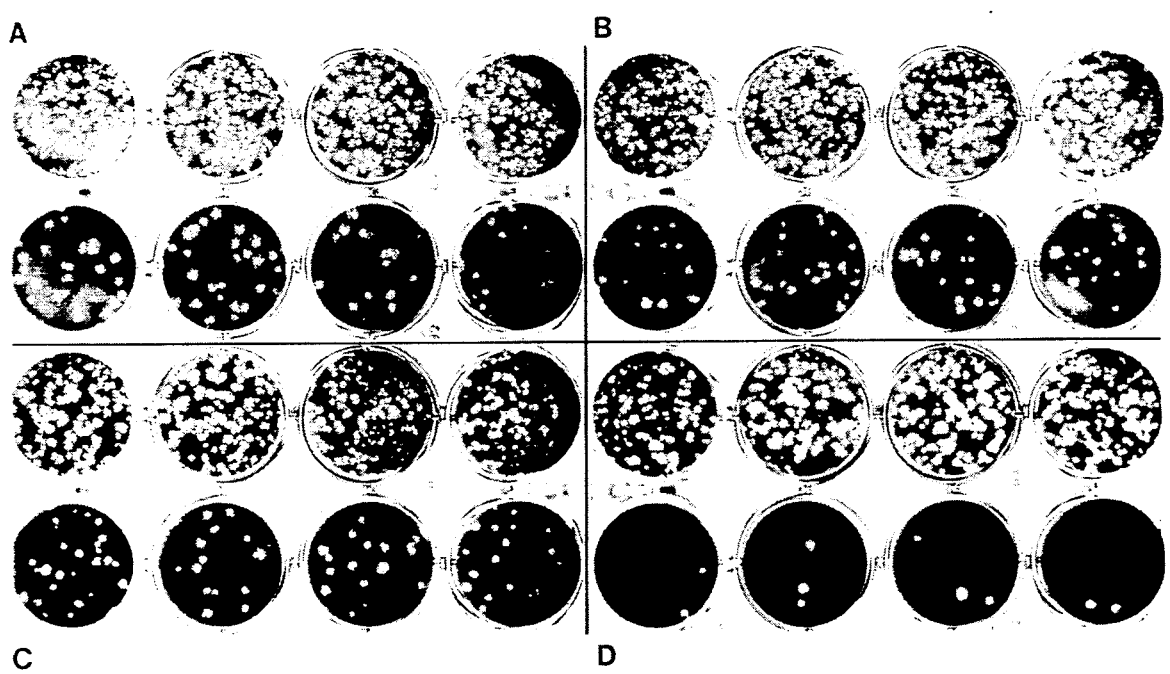
FIG. 1 is a photograph of four sets of eight cell monolayers on plastic dishes inoculated with Herpes Simplex Virus Type 1 (HSV) variously treated or untreated as will be described more fully hereinafter.

FIG. 1 shows sets of cultured cells grown as round films (cell monolayers) on plastic dishes. The cell monolayers were inoculated with Herpes Simplex Virus Type I (HSV). When active virus is present in the inoculum, the virus makes holes (plaques) in the cell monolayers. These appear as ragged, white areas in the dark monolayers. By counting the number of plaques, the number of active virus (plaque forming units or pfu) in the inoculum can be determined.

In each panel (A through D of FIG. 1), the top row of four cell monolayers was inoculated with a $10^{-2}$ dilution of HSV and not treated at all; the bottom row of four monolayers, in each quadrant panel, was inoculated with a $10^{-3}$ dilution of virus. HSV, at $10^{-3}$ dilution, was left untreated (bottom row of quadrant A), or was treated for 10 minutes at 23° C. with only 0.001% (wt/vol.) sodium dodecyl sulfate (SDS) (bottom row of quadrant B), with only 0.0025% (wt/vol.) glutaraldehyde (bottom row of quadrant C), or with a mixture of 0.001% (wt/vol.) SDS and 0.0025% (wt/vol.) glutaraldehyde (bottom row of quadrant D). In all cases, the exposure time was equal to 10 minutes at room temperature. Panels B and C show little or no reduction in the number of virus pfu compared to panel A. Panel D, however, shows an 80% to 90% reduction in virus pfu. Thus, at the concentrations used in this test, SDS and glutaraldehyde must be present together, and must work synergistically, to inactivate HSV Type I.

DETAILED DESCRIPTION OF THE INVENTION

To better understand why a combination of highly diluted glutaraldehyde with anionic surfactants displays more than an additive virucidal action, it is necessary to analyze and understand each mechanism of action of the two chemicals and determine how each affects the fundamental structure of viruses.

Without being bound to any particular theory, the following rationale is believed to be pertinent for an understanding of the effect of the virucidal compositions of the present invention.

First, consider the cidal mechanism of aldehydes in general and glutaraldehyde in particular. Aqueous aldehyde solutions have low concentrations of the pure aldehyde molecule, called the "monomer". This monomer, which is understood to be a single, simple, aldehyde molecule, is always present in equilibrium with larger, more complex, molecules referred to as "hydrates". Hydrates result from the condensation or polymerization of the small monomers into larger agglomerates. In any aldehyde solution, an equilibrium is believed to be quickly established between the relatively small monomers and the larger polymers or hydrates resulting in relatively stable concentrations of each. This equilibrium is based on variables which include the concentration of the chemical, pH, temperature, turbulence, and a variety of other factors.

The aldehyde monomer is the primary cidal agent in the aqueous aldehyde solution The cidal efficacy of any aldehyde containing formula (i.e., formaldehyde, glutaraldehyde, etc.) is directly related to the number of monomer molecules present at the time of use in the solution. The equilibrium between the monomer and the larger hydrates and polymers in both formaldehyde and glutaraldehyde aqueous solutions is illustrated in FIG. 2.

Figure 2:
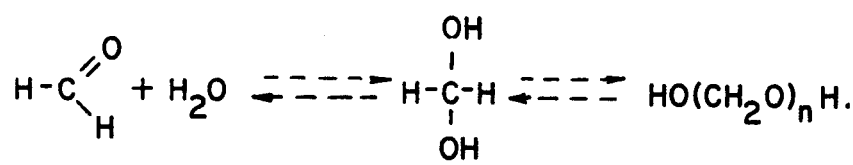
FIG. 2 is a symbolic depiction of the equilibrium between aldehyde monomer and larger hydrates and polymers.
Figure 2:
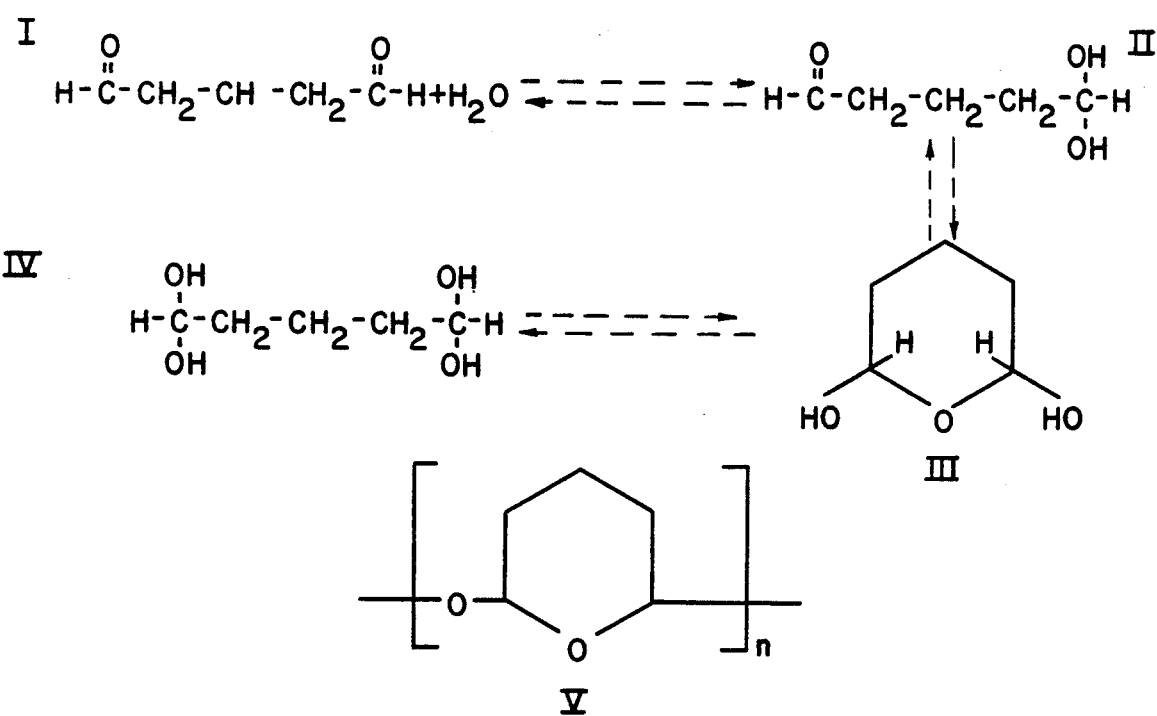

For glutaraldehyde, ($OHC-CH_2-CH_2-CH_2-CHO$), in aqueous alkaline solution, the monomer is in equilibrium with polymers of the Type II, III, and IV shown in FIG. 2. The formation of these polymers is irreversible and cannot return to the active monomer form, even with heating or ultrasonation. Both aging and alkaline pH greatly accelerate the formation of irreversible polymers. In other words, aging and alkalinity quickly decrease the cidal activity of glutaraldehyde solution. When in the acid range, the glutaraldehyde monomers have a slower rate of polymerization and are in equilibrium with Type V polymers which are reversible. This explains why acid glutaraldehyde solutions have a far longer biocidal life than alkaline solutions. This discussion can be supplemented by reference to the article Biocidal Mechanisms of Saturated Dialdehydes and their potentiation by ultrasound, Boucher, Last and Smith, Proc. West. Pharmacol. Soc. 16:282-288 (1973), incorporated herein by reference in its entirety.

Formaldehyde and glutaraldehyde, as well as other aldehydes, are alkylating agents. They can chemically react with sulfhydryl, hydroxyl, amino and carboxyl groups. Many such groups are present in the structural components of viruses and virion structures are highly susceptible to aldehydes. Studying the foot and mouth disease virus, Sanger et al (Journ. of Gen. Virology 21:399–406, 1973) were the first to show that glutaraldehyde produces considerable alterations in the arrangement of the RNA and protein subunits in this picornavirus. Also, Hopwood showed (Histochem. J. 7:267, 1975) that glutaraldehyde reacts more easily with RNA, i.e., at a lower temperature, than with DNA. Thus nucleic acids, as well as enzymes, proteins and lipids, all react with glutaraldehyde. The more common reactions encountered, however, are those involving amino groups which lead to protein cross-linking.

To better understand the virucidal action of the combination of aldehydes and anionic surfactants, we studied two different viruses: Herpes Simplex Virus Type 1 and Coxsackie Virus B6. Herpes Simplex Virus (HSV) Type 1 is a relatively fragile, DNA-containing virus (with an envelope); the Coxsackie Virus B6 is a naked (no envelope), resistant, RNA-containing virus.

The HSV virion is composed of three major structural features important to this invention: (1) a linear doublestranded DNA, (2) a symmetrical, protein shell known as the capsid, and (3) a surrounding, lipid-containing envelope. The capsid is composed of individual clusters of polypeptides (capsomers) which are coded by the virus. The envelope is derived from the nuclear membrane of the infected cell. This envelope contains lipids, carbohydrates and proteins. During virus replication, a number of enzymes such as DNA polymerases are present; when they are blocked, virus replication is inhibited. As previously mentioned, glutaraldehyde molecules can interfere with enzymes and DNA-binding proteins, but probably more readily reacts with structural proteins or the glycoproteins of the envelope.

The Coxsackievirus B6 is a smaller virus (24-30 nm) of cubic symmetry. This RNA virus does not have an envelope; it has 32 capsomers which fit together closely forming the capsid. The capsid appears to be very difficult to penetrate, thus protecting the nucleic acid core of the virus. Glutaraldehyde molecules may, therefore, need longer contact times to reach key internal polypeptides or nucleic acids which may be critical to virus inactivation.

Specific anionic agents, such as Sodium Dodecyl Sulfate (SDS), may contribute to the virucidal mechanism of aldehydes. This alkyl sulfate, SDS, has a strong negative charge; it has the following formula:

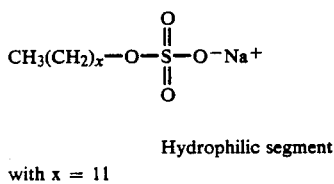

Hydrophilic segment with x = 11

The following sequence of events may take place when an enveloped virus is in the presence of SDS. First, the anionic agent binds to the membrane causing membrane lysis. The membrane is solubilized as anionic-lipid-protein complexes which are further solubilized to give SDS-protein complexes and SDS-lipid complexes. This mechanism was suggested by Simons et al (Membrane Protein and Their Interaction with Lipids, Ed Capaldi, Vol. 1, 207-2343, Marcel Dekker, NY, 1977). These authors worked with the Semliki Forest virus (SFV), an alpha virus in the Togaviridae. SFV contains a spherical nucleocapsid which is composed of one single-stranded RNA molecule and one lysine-rich protein species, the nucleocapsid protein, the latter is covered by a lipid membrane that is studded with glycoprotein surface projections. Lysis of the viral membrane begins at SDS concentrations of about $5 \times 10^{-5}$M. Dissociation of the nucleocapsid into RNA and protein takes place at SDS concentrations as low as $1 \times 10^{-4}$M. Free SDS concentrations of $0.75 \times 10^{-3}$M are sufficient for complete delipidation. This indicates that the whole sequence from lysis to delipidation occurs at SDS concentrations below the critical micellar construction (CMC). It is our contention that this extremely rapid physical destruction of viral envelopes is the key factor allowing the glutaraldehyde molecules to penetrate and inactivate viruses through specific reactions with enzymes, virion proteins or nucleic acid.

SDS, alone, can inactivate viruses through the mechanism previously described. For instance, in the case of Herpes Simplex Virus Type 1, F. Burnet and Lush (Australian J. Exp. Biol. and Med. Sci., 18:141-150, 1940) concluded that partial inactivation of HSV occurred at 0.002% (wt/vol.) SDS, while complete inactivation was observed with 0.005% (wt/vol.) SDS. This was confirmed in our recent study (see Table IV) which was conducted with a slightly modified EPA method and showed complete kill in 10 minutes with a SDS concentration of 0.005%. As shown by Burnet and Lush, more resistant viruses, such as Coxsackieviruses or Vacciniavirus (a DNA containing virus with a lipid containing complex coat), required higher concentration of SDS (0.025% wt/vol.) for complete virus inactivation.

The present invention demonstrates that the solubilization and dissociation of nucleocapsids by anionic agents such as alkyl sulfates enables the rapid penetration of active aldehyde radicals for further lethal action on key structural components of viruses. This "double action" cidal mechanism can be clearly seen from the results of the experiments reported in Tables III, IV, V, and VI.

TABLE III

Inactivation Study of Coxsackievirus B6 (CBV) Experiments conducted with Glutaraldehyde, Triethylene glycol, non-ionic (Tergitol 15-S-12) and anionic (SDS) surfactants.

| Treatment of Virus[1] | % Activity remaining after | | | |
|---|---|---|---|---|
| | 0 Min | 5 Min | 7.5 Min | 10 Min |
| No addition | 100 | | | 92 |
| TEG[2] | 100 | 100 | 100 | 100 |
| Terg. | 100 | 100 | 70 | 100 |
| SDS | 100 | 82 | 48 | 46 |
| TEG + Terg. | 100 | 100 | 100 | 100 |
| TEG + SDS | 100 | 100 | 100 | 100 |
| Glut | 100 | 100 | 85 | 90 |
| Glut + TEG | 100 | 100 | 100 | 96 |
| Glut + Terg. | 100 | 100 | 100 | 100 |
| Glut + SDS | 100 | 36 | 35 | 40 |
| Glut + TEG + Terg. | 100 | 100 | 86 | 72 |
| Glut + TEG + SDS | 100 | 45 | 42 | 12 |

[1] Experiments were done at room temperature in 1.0 ml reaction volumes. Procedure as described in patent.
[2] Concentrations used (wt/vol.):
Triethylene glycol (TEG): 0.04%
Tergitol (15-S-12): 0.05%
Sodium Dodecyl Sulfate (SDS): 0.05%
Glutaraldehyde (Glut): 0.006%

TABLE IV

Inactivation Study of Herpes Simplex virus (HSV) Type 1 Experiments conducted with Glutaraldehyde, non-ionic (Tergitol 15-2-12) and anionic (SDS) surfactants.

| Treatment of Virus | % Activity remaining after | |
|---|---|---|
| | 0 Min. | 10 Min. |
| 0.0006% Glut | 100 | 100 |
| 0.0006% Glut | 100 | 100 |
| 0.00125% Glut | 100 | 100 |

TABLE IV-continued

Inactivation Study of Herpes Simplex virus (HSV) Type 1
Experiments conducted with Glutaraldehyde,
non-ionic (Tergitol 15-2-12) and anionic (SDS) surfactants.

| Treatment of Virus | % Activity remaining after | |
|---|---|---|
| | 0 Min. | 10 Min. |
| 0.05% SDS | 100 | 0 |
| 0.005% SDS | 100 | 0 |
| 0.003% SDS | 100 | 3 |
| 0.001 SDS | 100 | 58 |
| 0.00075% SDS | 100 | 100 |
| 0.00050% SDS | 100 | 100 |
| 0.05% Terg | 100 | 0 |
| 0.04% Terg | 100 | 94 |
| 0.005% Terg | 100 | 49 |
| 0.0005% Terg | 100 | 100 |
| 0.00005% Terg | 100 | 100 |
| 0.0000006% Terg | 100 | 100 |
| 0.00125% Glut + 0.00075% SDS | 100 | 71 |
| 0.00125% Glut + 0.00100% SDS | 100 | 74 |
| 0.00125% Glut + 0.003% SDS | 100 | 9.4 |
| 0.00250% Glut | 100 | 80 |
| 0.00250% Glut + 0.0005% Terg | 100 | 50 |
| 0.00250% Glut + 0.0005% SDS | 100 | 32 |
| 0.00250% Glut + 0.00075% SDS | 100 | 38 |
| 0.00250% Glut + 0.001% SDS | 100 | 24 |
| 0.00250% Glut + 0.003% SDS | 100 | 4.7 |

Glut: Glutaraldehyde
SDS: Sodium Dodecyl Sulfate (anionic Surfactant)
Terg: Tergitol 15-S-12 ethoxylates of isomeric linear alcohols (non-ionic surfactant)

TABLE V

| Composition of Solutions | % HSV 1 activity remaining after a 10-minute contact time with: | | | |
|---|---|---|---|---|
| | SDS Alone | Glut Alone | Expected Additive Result | Actual Glut/SDS Results |
| 0.0005% SDS | 100 | | | |
| | | | 80 | 32 |
| 0.0025% Glut | | 80 | | |
| 0.00075% SDS | 100 | | | |
| | | | 80 | 38 |
| 0.0025% Glut | | 80 | | |
| 0.001% SDS | 58 | | | |
| | | | 38 | 24 |
| 0.0025% Glut | | 80 | | |

SDS: Sodium Dodecyl Sulfate (anionic surfactant)
Glut: Glutaraldehyde

TABLE VI

Influence of Triethylene Glycol (TEG) on the
Inactivation of Herpes Simplex Virus (HSV) Type 1
by Non-Ionic and Anionic-Glutaraldehyde Compositions

| Treatment of Virus (concentrations in % (wt/vol.)) | % Activity remaining after | |
|---|---|---|
| | 0 Min. | 10 Min. |
| 0.04% TEG | 100 | 100 |
| 0.04% TEG + 0.0005% SDS | 100 | 100 |
| 0.04% TEG + 0.0005% SDS + 0.0025% Glut. | 100 | 77 |
| 0.0005% SDS + 0.0025% Glut. | 100 | 32 |
| 0.04% TEG + 0.0005% Terg + 0.0025% Glut. | 100 | 100 |
| 0.0005% Terg + 0.0025% Glut. | 100 | 50 |
| 0.00075% SDS + 0.00125% Glut. | 100 | 71 |
| 0.00075% SDS + 0.00125% Glut. + 0.04% TEG | 100 | 100 |

TEG: Triethylene Glycol
SDS: Sodium Dodecyl Sulfate (anionic surfactant)
Terg: Tergitol 15-S-12 ethoxylates of isomeric linear alcohols (non-ionic surfactant)
Glut.: Glutaraldehyde Aldehyde formulations alone or with surfactants have very little practical value when applications require the elimination of either the odor or the irritation potential which are always present with aqueous aldehyde solutions. To eliminate odor and decrease the aldehyde aggressivity in liquid or vapor phase, we combined anionics and aldehydes with glycol type molecules. Through hydrogen bonding, glycol and aldehydes will form physical complexes (i.e., larger molecules) which exhibit a lower vapor pressure and less eye or skin toxicity. This method was first suggested by Trujillo and Lindell in 1973. It has been fully described both in U.S. Pat. No. 3,886,269 and in a paper entitled "New Formaldehyde Base Disinfectants" (J. Appl. Microb. 26 (1):106–110, July 1973) which deals with formaldehyde complexing with ethylene glycol, glycerol and propylene glycol. In 1973, Harriet Field of the Queen Mary Veteran's Hospital in Montreal, Canada, reported the elimination of glutaraldehyde vapors by complexing glutaraldehyde with propylene glycol and glycerol.

The direct complexing of a glutaraldehyde solution with triethyleneglycol was first reported by the inventor here in the summer of 1975. On Feb. 15, 1977, the first odorless commercial glutaraldehyde/triethylene glycol composition was approved by the USDA under the trade name AGROCIDE 2. A concentrate of this formula was later registered by the EPA on Feb. 2, 1979 under the Registration No. 15136-5. Between 1976 and 1977, H. D. Muller of the University of Georgia College of Agriculture released several reports describing the successful replacement of formaldehyde by glutaraldehyde/triethylene glycol solutions in applications in poultry hatcheries. The use of these triethylene glycol complexes in the hospital field was further reported by the inventor in the November 1978 (Respiratory Care 23 (11):1063–1072). The glutaraldehyde/triethylene glycol solutions used were potentiated with non-ionic surfactants as described in U.S. Pat. No. 3,968,.250, or by combinations of non-ionic with anionic surfactants. However, non-ionic, cationic and anionic surfactants behave differently and sometimes in opposing direction when they are in the presence of the key components of viruses (proteins, enzymes, and membranes). For instance, the cidal activity of anionic surfactants increases with decreasing pH value, while the opposite behavior is observed in the case of cationic surfactants, indicating that the first step in anionic interaction consists of an ionic absorption to membranes. This may result in cytolysis, autolysis, and the eventual inactivation of metabolic processes (see D. F. Hoelzl Wallach, The Plasma Membrane, Vol. 18, Heidelberg Science Library, Springer-Verlag, New York, 1972). In the case of proteins, non-ionic surfactants show either no interaction at all or interactions which are extremely weak, while anionics show very intense interaction with proteins and polymers Non-ionic surfactants generally do not inactivate or denaturate enzymes. Anionic surfactants, on the other hand, show strong inactivation and denaturation of enzymes, while cationic surfactants are generally less effective than anionic surfactants (M. J. Schwuger and F. G. Bartnik, ed. by C. Gloxhuber, Chapter 1, pp 32, M. Dekker, Inc., NY 1980). It was surprising, however, to discover that replacing cationics and non-ionics by specific anionics in glutaraldehyde-glycol complex solutions leads to different and more potent virucidal formulas than merely the additive effect of the two components.

To assess the influence on virucidal efficacy of the three key chemicals (glutaraldehyde, triethylene glycol, and anionic surfactant) used in the formulas of the present invention, we conducted a series of experiments with both the Coxsackie B6 virus and Herpes Simplex virus Type 1. Results of these experiments are given in Table III (CBV) and Table IV, (HSV 1).

The non-ionic surfactant (U.S. Pat. No. 3,968,248) used in our comparative study was a mixture of ethoxylates of isomeric linear alcohols manufactured by Union Carbide under the trade name TERGITOL 15-S-12. The structural formula of this non-ionic is as follows:

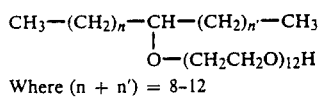

Where $(n + n') = 8-12$

Where $(n+n')=8-12$
There are from 11-15 carbon atoms in the hydrophobic portion of the molecule.

I. Coxsackievirus B6 studies:
A. The stock solution of Coxsackievirus B6 contained $5.17 (\pm 2.3) \times 10^5$ pfu/ml. The concentrations percent (wt/vol.) of reagents in the reaction mixtures were glutaraldehyde (0.006%), TERGITOL (0.05%), SDS (0.05%), and TEG (0.04%). Virus Aliquots were mixed with (1) glutaraldehyde with or without TEG, SDS or TERGITOL OR (2) glutaraldehyde plus TEG with or without SDS or TERGITOL, OR (3) SDS or TERGITOL.
B. The reaction mixture was incubated at room temperature for 10 minutes. The reaction was stopped by the addition of 0.1% (final concentration) of sodium metabisulfite. Serial 10-fold dilutions were made from each reaction mixture. The dilutions were kept cold in an ice bath.
C. Then, four 0.2 ml aliquots from each serial dilution were inoculated onto four confluent layers of MA104 cells (monkey kidney fibroblasts). After an hour of incubation at 37° C., the inocula were removed from each monolayer. An agar overlay was added to each monolayer. The agar overlay contained nutrients to support the cell monolayers while any surviving, viable viruses were replicating. Three days later virus plaques were counted, and the results of the experiments were recorded. This protocol differs from an AOAC test in that virus was present in solution and not on penicylinders, and the virus plaques are counted to quantitate the virus. In an AOAC test, the virus is dried on penicylinders prior to exposure to a disinfectant. Also, in an AOAC test, virus is quantitated differently; virusinfected monolayers are scored as positive (virus plaques are present) or negative (virus plaques are not present).

II. Herpes Simplex virus I studies:
A. The Herpes Simplex virus stock solution contained $2.48 (\pm 1.0) \times 10^5$ pfu/ml The virus stocks were mixed in one ml volumes with the various chemicals having final concentrations as shown in Table IV.
B. After 10 minutes at room temperature (22°-25° C.) serial 10 fold dilutions were made and inoculated onto four monolayers of cells per dilution (0.1 ml/monolayers).
C. The inoculated cells were incubated 60 minutes to allow virus attachment. Then the inoculum was removed, and an overlay of virus growth medium plus methylcellulose was added. Plaques formed five days later. To enhance visibility of the plaques, the cells were fixed with 0.5% glutaraldehyde and stained with 1.5% crystal violet. The plaques in each monolayer were counted and recorded.

One important feature of the present invention is the presence of glycol molecules in such a quantity that they eliminate most of the aldehyde odors while not decreasing or drastically affecting the virucidal efficacy of the glutaraldehyde anionic solution. There are few papers which pertain to the virucidal activity of glycols in liquid phase. Klein and Deforest reported (Disinfection, Sterilization, and Preservation, ed. S. S. Block, P. 432, Editor Lea and Fabiger 1983) that 100% propylene glycol inactivated 100% of Coxsackievirus B1, but only 99% (two logs) of Poliovirus 3 activity. Glycols alone, in dilute solution, have not been reported to be virucidal. Robertson et al. (Science, 97, 142-144, 1943) reported that glycols sprayed into a chamber (40 to 60% humidity), inactivated aerosolized influenza virus. These results have not been duplicated under field test conditions.

In our experiments (Tables III, IV) the triethylene glycol (TEG) was used as a liquid and not as an aerosol at very low concentrations (0.04%), and therefore contribution to virucidal action was not expected. With Coxsackievirus, no substantial increase or decrease in virucidal activity was observed after adding triethylene glycol (0.04%) to 0.006% glutaraldehyde. As theoretically expected, triethylene glycol alone, at a concentration of 0.04%, had no effect on the virus titer after 10 minutes. The same results were observed when using a 0.04% TEG with 0.05% non-ionic or anionic surfactant.

However, virucidal activity increased when glutaraldehyde/non-ionic and glutaraldehyde/anionic solutions were tested in the presence of 0.04% triethylene glycol. In all cases the glutaraldehyde/anionic solutions with or without glycol always showed greater virucidal action than the corresponding solutions with non-ionic surfactants.

Saitanu and Lund (Appl. Microbiol. 29(5):571-574) also studied the effect of glutaraldehyde on Coxsackievirus. They used 0.5% glutaraldehyde as the lowest test concentration. They reported a 90% loss in titer in 20 minutes a 99% loss in 30 minutes. Our data in Table III show that 0.006% glutaraldehyde (1/80th of the amount used by Saitanu and Lund) can result in a 60% loss in virus titer in 10 minutes if 0.5% SDS is present with the glutaraldehyde SDS, alone can reduce Coxsackievirus B6 titer; however, the kinetics of this reaction are slower than those of 0.006% glutaraldehyde plus 0.05% SDS. This clearly demonstrates the enhancement of virucidal activity which occurs when SDS is added, in small amounts, to low levels of glutaraldehyde.

The Coxsackievirus B6 study showed that we could deodorize, with the addition of the glycol, without destroying the activity of the dialdehyde/anionic compositions, the object of the present invention. However, it is important to stress that glycol concentrations in the final solution should remain lower than 590 per cent by weight if one wants to avoid a decrease in cidal activity. For example, Dr. Hopfer (Table VII), in 1982 at the University of Texas System Cancer Center in Houston, used commercial glutaraldehyde concentrates (25 and 50%: by weight) and showed that there was a loss in cidal activity after adding a substantial amount of glycol. The analytical method used in these tests was the sporicidal AOAC test. Far smaller percentages of glycol were and are to be used in the formula object of the present. It was therefore extremely important to show that these small percentages of glycol will not substantially affect the virucidal efficacy of our compositions.

TABLE VII

SPORICIDAL ACTIVITY OF 50% (wt/vol.) POTENTIATED GLUTARALDEHYDE AND TRIETHYLENE-GLYCOL AT ROOM TEMPERATURE AOAC Method 4015–4017
Test Organism: *Clostridium Sporogenies* ATCC 3584
Carrier: Penicylinders

| Test Solutions | Number of Positive Tubes/ Total Tested |
|---|---|
| Glutaraldehyde 50% | 0/20 |
| Glutaraldehyde 25% | 1/20 |
| Glutaraldehyde 25% + Triethylene Glycol 50% | 10/20 |
| Triethylene Glycol 100% | 20/20 |

Other glycols could be used to deodorize and decrease the aggressivity of aldehydes; however, triethylene glycol (TEG) was chosen because it is completely soluble in aqueous glutaraldehyde solutions. Repeated-dose oral toxicity studies have shown that TEG is safer than ethylene and diethylene glycols. Eye irritation tests have also shown that it is less irritating than propylene glycol. In our examples we have used between 6.6 (CBV) and 16 times (HSV) more TEG than glutaraldehyde. However, complementary tests have shown that odor elimination of aldehydes can take place using TEG to glutaraldehyde ratios equal to one or slightly higher. Therefore, to practice this invention, the amount of triethylene glycol added to the formula maximizes odor elimination. This amount should either be equal to but not less than the glutaraldehyde percentage present in the aqueous solution.

If one looks now at the data pertaining to the Herpes Simplex virus type 1 experiments (Table IV and V), one will find that the virucidal effect of low concentration mixtures of glutaraldehyde and sodium dodecyl sulfate are far superior to the added virucidal effects of each separate chemical. The same thing had also been previously demonstrated in the case of the more resistant Coxsackievirus B6. However, in the case of HSV 1, the addition of TEG to the glutaraldehydesurfactants mixture did not increase the cidal activity of this formula but slightly decreases it (Table VI). With Coxsackievirus, the ternary mixture containing the anionic agent was always more virucidal than the corresponding composition containing the non-ionic surfactant.

The modest decrease in virucidal action due to the addition of diluted glycols was small enough not to affect the many uses of these deodorized solutions.

Another important advantage from the use of anionic surfactants according to this invention is the fact that, contrary to non-ionics and cationics, they quickly combine with polymers and glycols. In the case of polyethylene glycol, for instance, it has been demonstrated by S. Gravsholt (Proc. Scand. Symp. Surf. Active Agents 132–136, 1965) that SDS can be easily bound to this molecule. Therefore, the preparation of virucidal solutions containing, for instance, the three following chemicals, glutaraldehyde, triethylene glycol, and sodium dodecyl sulfate, is extremely easy since TEG and SDS dissolve in a matter of minutes into an aqueous solution of acid glutaraldehyde under mild agitating conditions at room temperature.

As previously explained, the pH of the ternary solutions is extremely important since it defines (Boucher, Proc. West Pharmocol Soc. 16:282–288, 1973) the amount of free dialdehyde monomers available to combine with the critical molecules of the viral structure. All experiments conducted with solutions having a pH higher than 7.5 or lower than 4.2 showed less virucidal activity. The preferred range being 7.2 to 4.5. Such a trend had been previously observed by Saitanu and Lund when studying the activity of glycolless glutaraldehyde solutions with a Coxsackievirus B3 (Appl. Microb. 29 (5):57–574 May 1975). The buffer salts of the following chemicals and chemical combinations have been successfully used with the ternary compositions object of the present invention: monobasic potassium or sodium phosphate with anhydrous dibasic sodium phosphate, maleic acid, trisodium citric acid, citrate-phosphate buffer, succinic acid, cacodylate buffer, n-(2-acetamido) iminodiacetic acid, piperazine-n, $n^1$-bis(2-ethanesulfonic acid), 2(n-morpholino)ethane sulfonic acid, with pKa ranges from 4.2 to 7.2.

Two of the main advantages of the formula object of the present invention are the aldehydes odor elimination and the low level of irritation when they are used topically. The bonds between glycol and aldehydes monomers appear to be strong enough to decrease the solution vapor pressure, but they do not greatly affect the aldehydes reaction state as long as the total content of triethylene glycol is not higher than 10 to 25% by weight.

To assess the potential of the described compositions as a skin antiseptic, we conducted some skin irritation tests with the composition used for the Coxsackievirus B6 study (see Table III). The EPA- and FDA-approved method enables us to calculate the primary skin irritation score (PSI) following a single application to the intact skin of New Zealand White Rabbits. The scoring code (see T. Soc. Cosmet. Chem. 13 (6):281–289, 1962) ranges from 0 (non-irritating) to 8.0 (extremely irritating). The three lowest ratings are nonirritating (0.00–0.09), minimally-irritating (0.10–0.50) and slightly irritating (0.51–1.50). The Table III formula falls in the non-irritating category. Another study was also conducted with th- same formula to evaluate the vaginal irritation potent&al with the standardized FDA method. Treatment of vaginal mucosa with the Table III formula did not cause any significant mucosal irritation. Regarding eye irritation, we used the EPA test (40 CFR 163.81–4) and the formula was considered as non-irritating after 72 hours of exposure. All the above-mentioned tests indicate that the highly diluted virucidal formulas of the present invention exhibits a toxicity level as low or even lower than most antiseptics and prep-scrubs based upon iodophors, quaternary ammonium compounds, chlorhexidine gluconate and alcoholic solutions.

It is also possible for the composition of the present invention can contain lower alkanols such as methanol, ethanol, isopropanol and the like. A mixture of both could also be used. These minor modifications in the composition of the solvent will be dictated by the nature of the applications: decontamination of instruments, inanimate or animate surfaces, skin degerming, wound cleaning, and the like.

Although several specific examples of the inventive concept have been described for purposes of illustration, the invention concept have been described for purposes of illustration, the invention should not be construed as limited thereby nor to the specific features mentioned therein except as the same may be included in the claims appended hereto interpreted in view of the pertinent prior art. It is also understood that changes, modifications, and variations may be made without departing from the spirit and scope of the present invention.

I claim:

1. A method of deactivating viruses on an animate or inanimate surface which comprises applying to said surface an effective amount of a virucidal liquid composition comprising:
   (a) A solvent consisting of water or a lower alkanol;
   (b) A saturated monoaldehyde or dialdehyde containing from 2 to about 6 carbon atoms;
   (c) An anionic surfactant with a negatively-charged hydrophilic group selected from the group consisting of alkyl sulfates, alkyl sulfonates, alcohol sulfates, alkyl aryl sulfonates, dialkyl sulfosuccinates, and mixtures thereof;
   (d) Buffer salts in sufficient amounts to stabilize the Ph of the virucidal solutions inside the range of from about 4 to about 7.4 wherein the ratio by weight of anionic surfactant to dialdehyde is no less than about 1 to 4 and no more than about 10 to 11.

2. The method of claim 1 wherein (b) is a dialdehyde.

3. The method of claim 2 wherein said composition further comprises an odor-reducing agent selected from the group consisting of ethylene glycol, propylene glycol, diethylene glycol, triethylene glycol, polyethylene glycol, polypropylene glycol, and mixtures thereof.

4. The method of claim 3 wherein said odor-reducing agent is triethylene glycol.

5. The method of claim 3 wherein the maximum amount of glycol comprises between about 10% to about 20% by weight based on the weight of the solution.

6. The method of claim 3 wherein the weight of glycol compounds to dialdehyde is a ratio between about 1 to about 32.

7. The method of claim 3 wherein the aldehyde is present in concentration of from about 0.00125% to about 13.85% w/v, the glycol is present in a concentration of from about 0.00125% to about 20.7% w/v and the anionic surfactant is present in a concentration of from about 0.0005% to about 12.61% w/v.

8. The method of claim 2 wherein said dialdehyde is glutaraldehyde.

9. The method of claim 2 wherein said anionic surfactant is an alkyl sulfate.

10. The method of claim 2 wherein said anionic surfactant is sodium dodecyl sulfate.

11. The method of claim 2 wherein said composition is buffered in the 6.2 to 6.4 Ph range.

12. The method of claim 2 which comprises applying said composition to an inanimate surface contaminated by viruses.

13. The method of claim 2 which comprises destroying viruses by scrubbing contaminated skin with said composition.

14. The method of claim 13 wherein said composition further comprises an odor-reducing agent selected from the group consisting of ethylene glycol, propylene glycol, diethylene glycol, triethylene glycol, polyethylene glycol, polypropylene glycol, and mixtures thereof.

15. The method of claim 2 which comprises cleansing a virus contaminated wound by applying thereto said composition.

16. The method of claim 15 wherein said composition further comprises an odor-reducing agent selected from the group consisting of ethylene glycol, propylene glycol, diethylene glycol, triethylene glycol, polyethylene glycol, polypropylene glycol, and mixtures thereof.

* * * * *